(12) United States Patent
Rittmann

(10) Patent No.: US 6,270,512 B1
(45) Date of Patent: *Aug. 7, 2001

(54) INTERNAL NASAL DILATOR

(76) Inventor: Jean V Rittmann, 4700-176th St. SW. #A303, Lynnwood, WA (US) 98037

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/371,893

(22) Filed: Jul. 6, 1999

Related U.S. Application Data

(63) Continuation-in-part of application No. 09/010,943, filed on Jan. 22, 1998, now abandoned.

(51) Int. Cl.[7] .................................................. A61M 29/00
(52) U.S. Cl. ...................................... 606/199; 128/207.18
(58) Field of Search ....................... 606/199; 128/204.12, 128/207.18, 200.24; 623/10

(56) References Cited

U.S. PATENT DOCUMENTS

| | | | | |
|---|---|---|---|---|
| 851,048 | * | 4/1907 | Woodward | 606/199 |
| 1,481,581 | * | 1/1924 | Woodward | 606/199 |
| 1,597,331 | * | 8/1926 | Thurston et al. | 606/199 |
| 5,350,396 | * | 9/1994 | Eliachar | 606/199 |
| 5,479,944 | * | 1/1996 | Petruson | 606/199 |

* cited by examiner

*Primary Examiner*—Michael Buiz
*Assistant Examiner*—Kevin Truong

(57) ABSTRACT

A dilator/insert internally support the lateral nasal walls and securely stay in place without discomfort. It stays inserted by a pair of ledges (9a and 10a) and/or catches (7a and 8a), each resting behind a respective: limen nasi ridge (a somewhat vertical central protuberance on a lateral nasal wall); and/or a foot of the columella (the 'meaty' protuberance peripherally off the base of the columella). The insert is confined from shifting off those protuberances by being tall (distance between 1a and 2a); almost as tall near the entrances of the nose as the entrances themselves. When worn, the bridge (1a and 2a)/leg (3a, 4a an 5a, 6a) assemblies look like two central nose rings. The peripheral rigidity of the bridge/leg assemblies braces the lateral walls of the nose apart and keeps the ledges in position. Catches can position midway rearward on bottom legs; and they extend centrally enough to rest behind, without engaging, the feet of the columella. The function of the described embodiment is to improve nostril breathing. It, or a similarly functioning embodiment, assembled by incorporating nasal tubing can be used to keep nasal tubing in the nostrils and prevent such tubing from scraping the nasal walls. An embodiment of the insert can be used as comfortable nasal jewelry.

9 Claims, 4 Drawing Sheets

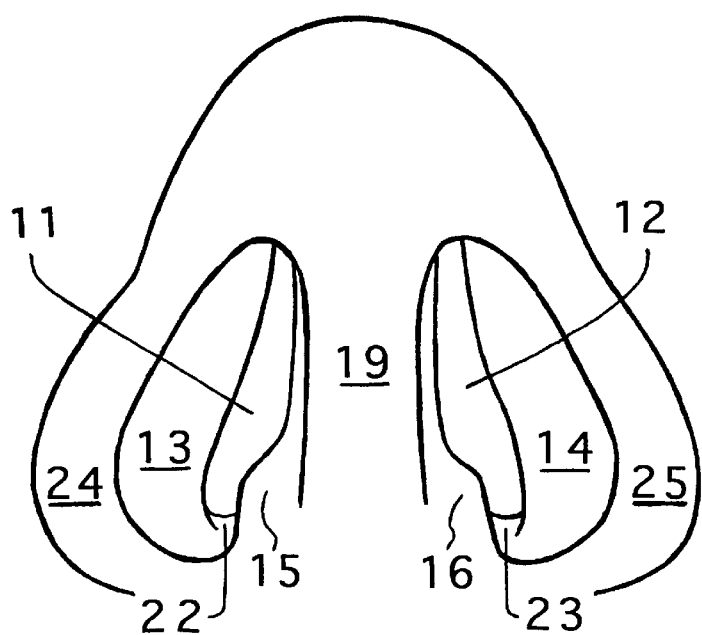
FIG. 2B
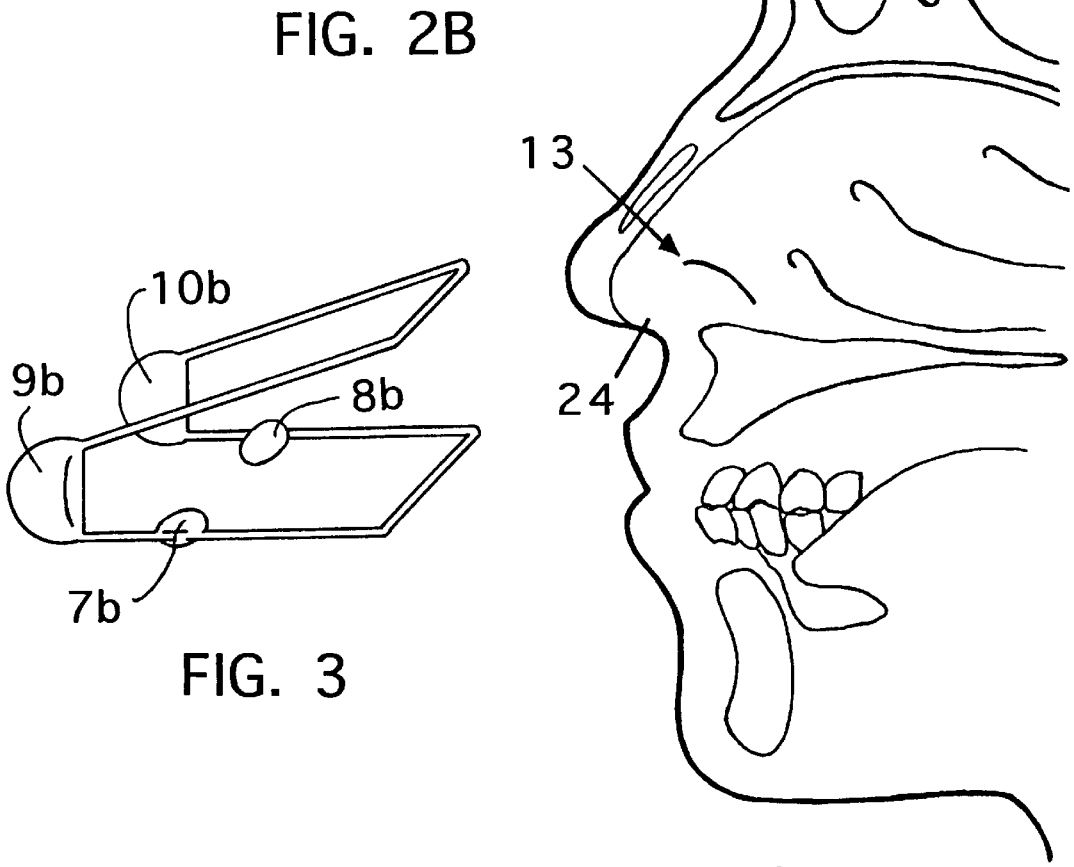
FIG. 3
PRIOR ART
FIG. 2A

INTERNAL NASAL DILATOR

This application is a CIP of application Ser. No. 09/010,943 filed Jan. 22, 1998, now abandoned.

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO MICROFICHE APPENDIX

Not Applicable

BACKGROUND OF INVENTION

This invention relates to nasal dilators. More specifically, to insertable nasal dilators. This invention also relates to breathing apparatus and accessories.

Many people routinely have difficulty breathing thru the nostrils, like while sleeping. Often this can lead to breathing thru the mouth. Breathing thru the mouth while sleeping can lead to snoring.

Snoring happens because, once asleep, our muscles go limp, including the nasal walls, the jaw, tongue, and throat. This can lead to the collapse of the nasal walls, breathing thru the mouth, and the tongue falling back in the throat. The 'snore' sound is often the tongue or nose vibrating as one attempts to breathe.

Prior-art external nasal strips can expand the nasal passages for improved breathing. They have many disadvantages: They are expensive. Each strip is only good for one use. Strips can be uncomfortable to remove. Strips often leave adhesive residue on the nose after removal. Strips can be time-consuming to remove (especially if company is at the door). Strips excessively expand the nasal cavities. Strips can leave nose sore. Breathing problems, like snoring and sleep apnea, are often 365-day-a-year problems. The expense, skin irritation, and discomfort of adhesive nasal strips can discourage daily use.

Because the nasal trips are external, they must open up a large length of the nasal cavities, even though usually only a small portion of the nose normally collapses during breathing.

Prior art nasal inserts include: U.S. Pat. No. 5,727,543 by Lugi Corsaro, granted Mar. 17, 1998 entitled NASAL BREATHING DEVICE; U.S. Pat. No. 1,255,578 by George Boxley, granted Feb. 5, 1918 entitled NASAL APPLIANCE; U.S. Pat. No. 1,481,581 by H. R. Woodward, granted Jan. 22, 1924, entitled NOSTRIL EXPANDER; U.S. Pat. No. 5,479,944 by Bjorn Petruson, granted Jan. 2, 1996 entitled NASAL DEVICES; U.S. Pat. No. 4,414,977 by Saeed Rezakhany, granted Nov. 15, 1983 entitled NASAL DILATOR; U.S. Pat. No. 4,201,217 by Robert L. Slater, granted May 6, 1980 entitled NOSTRIL EXPANDER; U.S. Pat. No. 4,759,365 by Leo Askinazy, granted Jul. 26, 1988 entitled SPRING COIL WIRE DEVICE; and U.S. Pat. No. 3,710,799 by Carlos Ramos Caballero, granted Jan. 16, 1973 entitled NOSE DILATOR. To stay in the nose, all the above inventions depend on tension to the lateral nasal walls, the septum, the floor of the sills, and/or the 'lips' of the external nares (external openings into the nose). The lateral walls slope down and outwards, promoting a device to slip out. The 'lips' of the external nares are slight and vary tremendously in size and shape from person to person. The 'lips' provide inadequate support. Most of the above inventions also greatly distort the shape of the nostrils and have a displeasing appearance when worn.

Breathe Relief™, item #41600 as distributed by HealthHouse USA Inc., P.O. Box 9034 Jericho, N.Y. 11753, has a pair of bulbs that fit into the hollow crevices of the nose-tip. These bulbs lift the lateral nasal walls by supporting against the sensitive septum. Breathe Relief relies on ineffective friction to try and keep it from slipping out of the nose-tip. The device can easily fall down/out of place, actually obstructing the airway.

Corsaro's device engages a longer and deeper portion of the septum than Breathe Relief™. It engages the septum, post of the columella, lateral walls, and (though not disclosed) the sill floor in the same manner as Boxley. That is, Corsaro's bridge 20; stop member 28; and first, second, and third members (42,44, and 46) match to Boxley's 1,2,3,10 and 9 respectively. Corsaro engages the uppermost portion of the columella [verifiable by noting his first wires and bridge position above second wires, and 44 positions left in all drawings].

Corsaro shows septal engagement in his FIGS. 5 and 6, even though the distance between first wires is too wide ($\approx$6.5 mm base, 9.5 mm top) to contact the thin ($\approx$2 mm) septum. True septal contact would require substantial wire flexibility not provided by the specified 1 mm stainless wire. Also, though not disclosed, Corsaro's third wire members are positioned to brace against the floor of the sills (same as Woodward's 1b; Petruson's "convexly curved edge"; and Boxley's 9). Sill and septal engagement can be uncomfortable.

CPAP and oxygen delivery are often provided thru nasal tubing. Nasal tubing is supported in the nares by a variety of apparatus. One such method of support is U.S. Pat. No. 5,477,852 by Robert M. Landis, granted Dec. 26, 1995 entitled NASAL POSITIVE AIRWAY PRESSURE APPARATUS AND METHOD. This method is complicated and inefficient. Another method is continuous tubing, with a pair of cannulae insertable into the nares. Cannulae are held in place by wrapping the tubing over the ears and securing it under the neck with a sliding tie. The cannulae may shift side-to-side in the nares, especially when sleeping. This shifting can cause internal scraping and irritation of the nasal walls.

Anatomy Terminology of the Nose

FIG. 2B depicts the inferior view of a human nose. The following terms, referred to throughout my text, may not be found in a dictionary:

columella (19): the external post, or column, of the septum feet of the columella*(15 and 16): the posterior protuberances of the columella limen nasi ridges (13 and 14)(and 13 in FIG. 2A): internal ridges of the lateral nasal walls (between the vestibule and atrium of each nare)

external nares (24 and 25)(and 24 in FIG. 2A): the external openings to the nose floor of the sills (22 and 23) floor of the nares

BRIEF SUMMARY OF THE INVENTION

My dilator/insert internally supports the lateral nasal walls and securely stays in place without discomfort. It stays inserted by a pair of ledges and/or catches, each resting behind a respective: limen nasi ridge (a somewhat vertical central protuberance on a lateral nasal wall); and/or a foot of the columella (the 'meaty' protuberance laterally off the base of the columella). The insert is confined from shifting off those protuberances by being almost as tall near the entrances of the nose as the entrances themselves.

An embodiment may have separate top and bottom bridges, each having a pair of opposite-side rearward legs for rearwardly inserting into a respective nare. The distance between top and bottom legs is frontwardly tall (near the nose entrances). When worn, the bridge/leg assemblies look like two central nose rings. Ledges can rearwardly mate top and bottom respective-side legs. Each ledge has a peripherally protuberancing surface to rest behind a respective, somewhat straight and vertical, limen nasi ridge. The lateral support of the bridge/ leg assemblies braces the lateral walls of the nose apart and keeps the ledges in position. When both ledges and catches are part of an embodiment, catches position midway rearward on bottom legs; and they extend centrally enough to rest behind, without engaging, the feet of the columella.

The function of the described embodiment is to improve nostril breathing. It, or a similarly functioning embodiment, assembled by incorporating nasal tubing, can be used to keep nasal tubing in the nostrils and prevent such tubing from scraping the nasal walls. As nasal jewelry, an embodiment may have catches and no ledges, where the catches rearwardly mate top and bottom respective-side legs; legs that are substantially half the length of an embodiment with ledges.

ADVANTAGES OF THE INVENTION

My nasal insert can be a one-time purchase, one-size can fit all, it is easy to remove, it can barely be felt, it stays securely in place, and it can stay in place without discomfort. It minimally expands the nasal walls so they will not dry out. Aesthetically it can look like the wearer has two nose rings, sometimes barely visible. It can be made with non-irritating materials. It can be inexpensive to manufacture. Plating it in gold or silver can give it value purchase appeal.

BRIEF DESCRIPTION OF THE DRAWINGS

FIG. 2A is a prior-art left-hand side view of a human nose, showing the a interior side of the right lateral nasal wall FIG. 2B is an inferior view of a human nose FIG. 3 is an embodiment of my nasal insert, side perspective view, with bulbous ledges and catches

Figure 7:
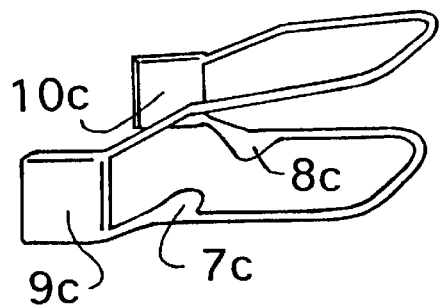
FIG. 7 is an embodiment of my nasal insert, side perspective view, with flat and bent ledges and bent legs
Figure 10:
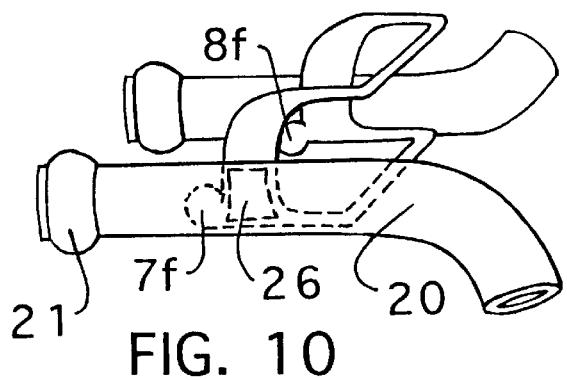
FIG. 10 is an embodiment of my nasal insert, side perspective view, with prior art adhesive and tubing
Figure 8:
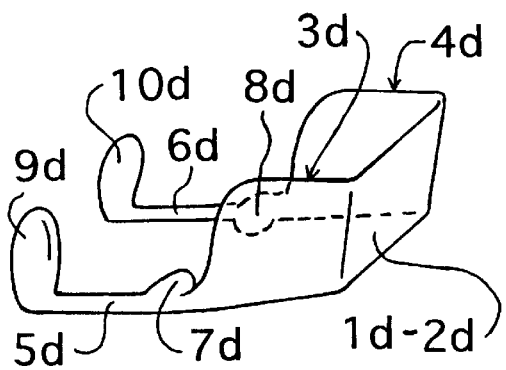
FIG. 8 is an embodiment of my nasal insert, side perspective view, with phantom leg tops and a planarly solid bridge
Figure 11:
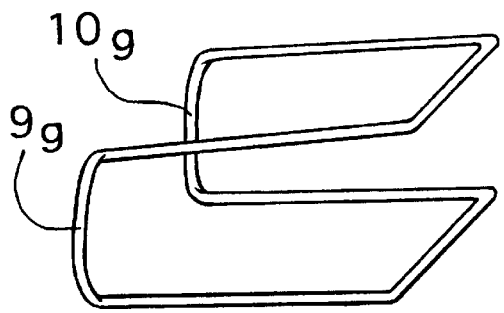
FIG. 11 is an embodiment of my nasal insert, side perspective view, without catches and with wire-tin ledges
Figure 9:
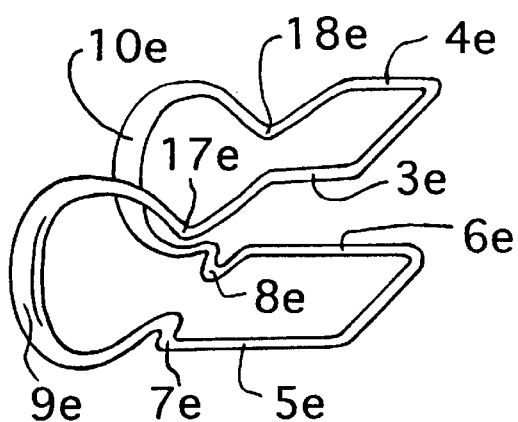
FIG. 9 is an embodiment of my nasal insert, side perspective view, with curving surfaces
Figure 12:
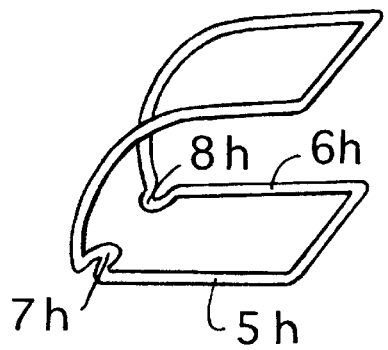
FIG. 12 is an embodiment of my nasal insert, side perspective view, without ledges

DESCRIPTION OF THE NOTATIONS 1 top of bridge
2 bottom of bridge
3 top right-hand-side leg
4 top left-hand-side leg
5 bottom right-hand-side leg
6 bottom left-hand-side leg
7 right-hand-side catch
8 left-hand-side catch
9 right-hand-side ledge
10 left-hand-side ledge
11 right-hand-side airway
12 left-hand-side airway
13 right-hand-side limen nasi ridge
14 left-hand-side limen nasi ridge
15 right foot of the columella
16 left foot of the columella
17 right cosmetic curvature on an embodiment
18 left cosmetic curvature on an embodiment
19 the columella
20 prior art tubing
21 sculpted ring added to prior art tubing
22 right-hand-side sill
23 left-hand-side sill
24 right-hand-side external nare
25 left-hand-side external nare
26 prior art adhesive
Letters after Notation Numbers Identifies Specific Embodiment
a identifies notations for the embodiment of FIG. 1
b identifies notations for the embodiment of FIG. 3
c identifies notations for the embodiment of FIG. 7
d identifies notations for the embodiment of FIG. 8
e identifies notations for the embodiment of FIG. 9
f identifies notations for the embodiment of FIG. 10
g identifies notations for the embodiment of FIG. 11
h identifies notations for the embodiment of FIG. 12

DESCRIPTION OF THE INVENTION

1. Breathing Obstructions—The Close of the Nose

Modern breathing problems include breathing while awake, snoring, and sinus problems. My nasal insert relates more to the first two. More specifically, my nasal insert supports the specific area of tissue or cartilage that closes the nose.

The airways (11 and 12 in FIG.2B) are visibly narrow. My nasal insert supports the nose open at its most narrow and most collapsible area: the nose's limen nasi ridges (13 and 14 in FIG. 2B, and 13 in FIG. 2A). The original function of the limen nasi ridges might well have been to seal the nose (from dust storms or water when swimming) by tensing one's nasal muscles. Modern humans rarely have a need for this function. Nowadays weakened nasal cartilage, like from injury or cosmetic surgery, appears to allow these ridges to close the nasal airway during normal breathing. Also, during sleep, relaxed nasal muscles and mucus-clogged vestibule hairs appear to allow these ridges to close the nasal airway.

Examine any anatomic illustration of the lateral nasal wall, behind the conchae*. One can see the limen nasi ridges are the only protrusions that obstruct nasal air flow. The least invasive way to improve nasal breathing, except some sinus problems, appears to be to support just the limen nasi ridges from narrowing the airway; and/or virtually closing the nose.

2. Description of One Embodiment of the Invention

Figure 1A:
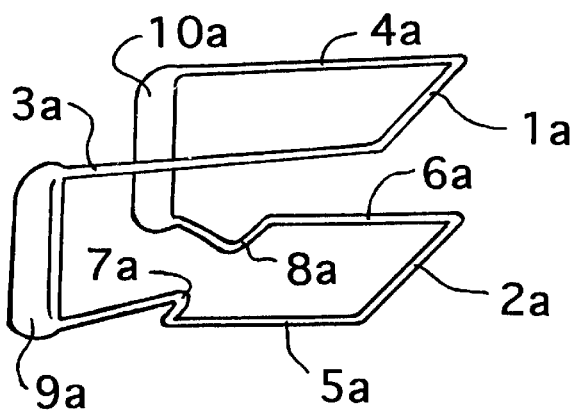
FIG. 1A is an embodiment of my nasal insert, side perspective view

One embodiment of my nasal insert is shown in FIG. 1A. The insert has a top (1a) and a bottom (2a) bridge. Each bridge has a pair of opposite side edges. A pair of top legs (right: 3a, and left: 4a) are fixedly and rearwardly attached to a corresponding opposite side edge of the top bridge. A pair of bottom legs (right: 5a, and left: 6a) are fixedly and rearwardly attached to a corresponding opposite side edge of the bottom bridge. The insert has catches (7a and 8a) protruding centrally and positioned near mid-length of each bottom leg. The insert has a pair of ledges (9a and 10a). Each ledge is fixedly attached on the rearward end of a corresponding top and bottom leg (attached downwardly from a top leg and upwardly from a bottom leg). The ledges support the bridge/leg assemblies vertically apart. The frontward ledge edges protrude slightly peripherally. This embodiment can be a one-size-fits-all version.

The catches in this embodiment appear as kinks in the wire-like legs. The bridge/leg connection is quite angular. The central surface of the catches and the peripheral surface of the ledges are smooth for comfort, when worn. In this embodiment the top of the bridge (1a) is narrower than the bottom bridge (2a).

Figure 1B:
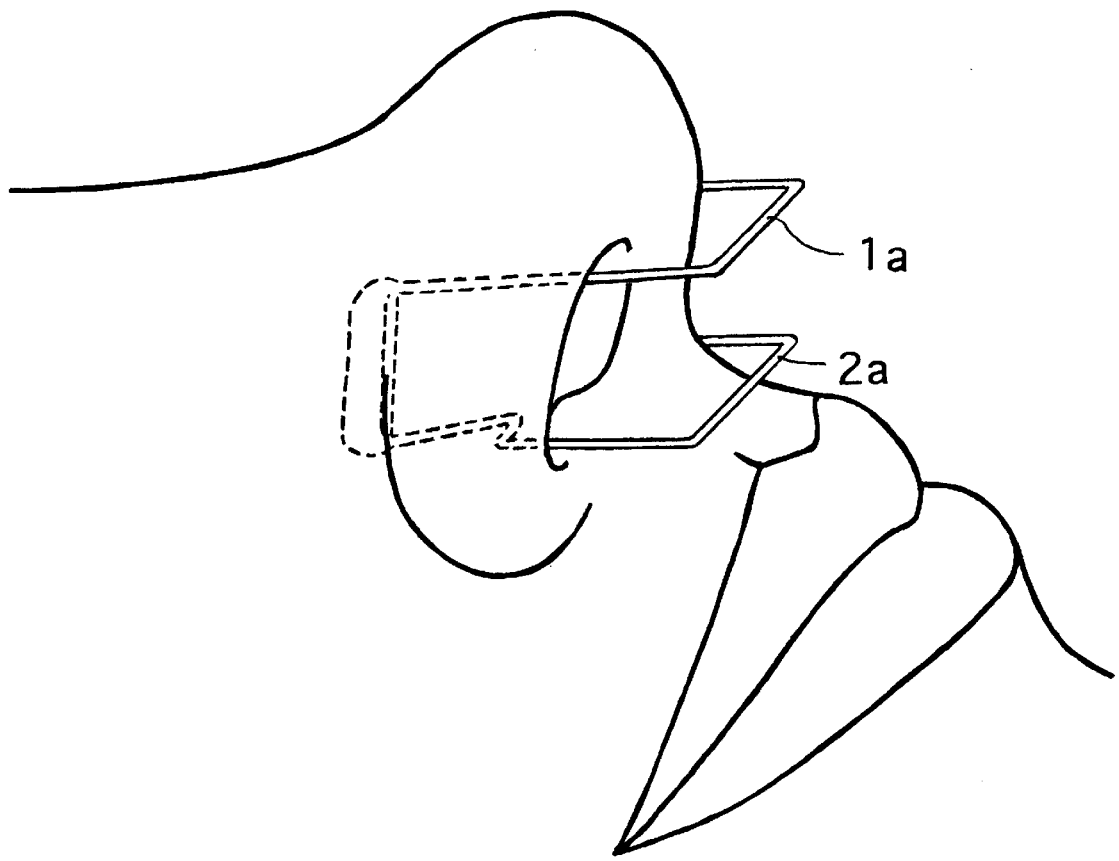
FIG. 1B is an embodiment of FIG. 1A in a wearer's nose, same perspective view
Figure 4:
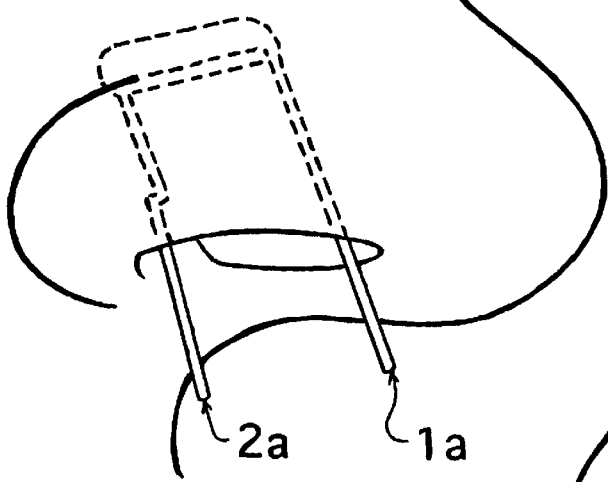
FIG. 4 is the embodiment of FIG. 1A in a wearer's nose, right-hand-side lateral view

The embodiment of FIG. 1A is shown in a wearer in same perspective view in FIG. 1B, and in right-side/lateral view in FIG. 4. The bridges (1a and 2a) externally transcend/position inferior to the wearer's columella On a one-size version, the top and bottom bridges may extend at different lengths away from the columella, depending on the individual wearer. The height from the frontward ends of respective top and bottom legs is nearly as tall as the nare entrances. The bottom legs near the bottom bridge (2a) can rest on the lip portion of the external nares. It is most comfortable when the bridge does not touch the wearer's columella.

Figure 5:
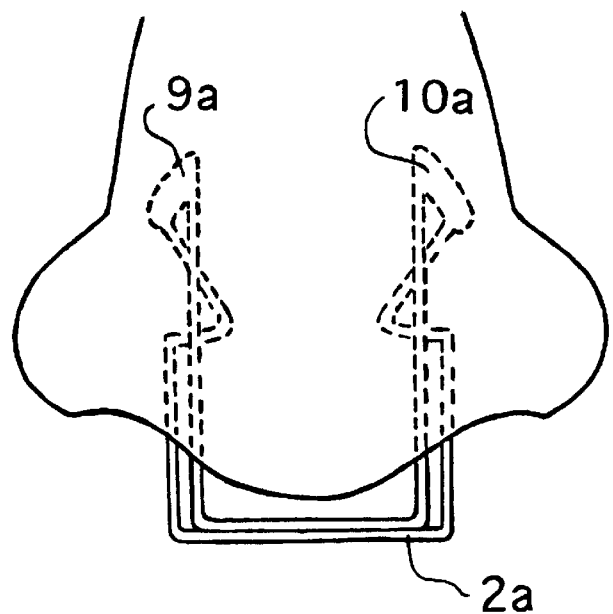
FIG. 5 is the embodiment of FIG. 1A in a wearer's nose, anterior view

The embodiment of FIG. 1A is shown in a wearer, front/anterior view, in FIG. 5. The bottom bridge is notated (2a). The ledges (9a and 10a) visibly narrow rearwardly (rear faces up in this figure) to tailor with the slope of a wearer's lateral nasal walls.

Figure 6:
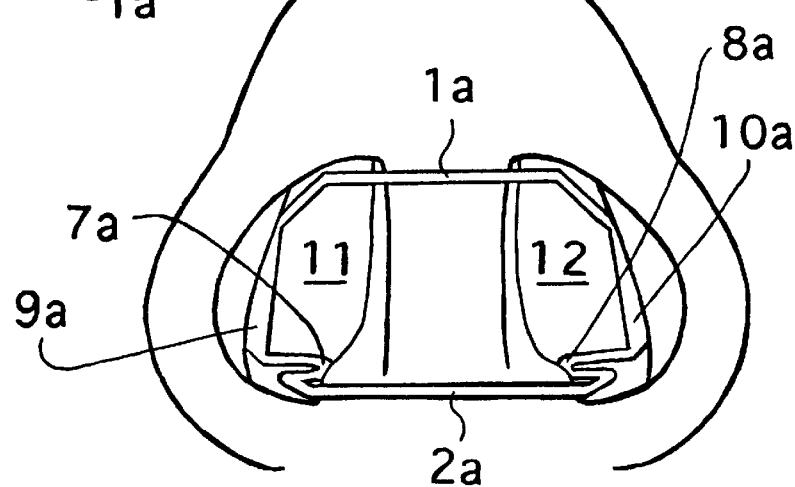
FIG. 6 is the embodiment of FIG. 1A in a wearer's nose, inferior view

The embodiment of FIG. 1A is shown in detail in a wearer, inferior view, in FIG. 6. The bridges (1a and 2a) cross between the nares, transcending the columella. The distance between the bridges (and the distance between the frontward ends of respective top and bottom legs) is substantially the anteroposterior (top to bottom) length of an external nare opening. The catches (7a and 8a) catch behind (the interior side of) the feet of the columella. The ledges (9a and 10a) catch behind/interior-to the limen nasi ridges.

The rearward (ledge) end of the embodiment's legs have been spread slightly peripherally for pictorial clarity in this FIG. 6. The effect of this spreading extra-enlarges the airway. Spreading the legs may be preferred by sinus, allergy, cold sufferers and those with large nares.

The ledges pressing against the angled lateral nasal walls prompts the insert outward, which keeps the catches against the interior side of the feet of the columella. The catches and ledges keep the insert in the nose. The space between respective top and bottom legs is substantially open to allow for breathing. The airway (11 and 12) is maximally between the top and bottom legs. Both the ledges, and the rearward portion of the legs, touch and support, or lift, the ridges to keep the airway open. There is minimal nasal distortion, and the nasal insert is extra-secured in the nose, when the ledges catch behind/interior-to, as compared to on, the ridges. The ledges lift the ridges by way of lateral support of the leg/bridge assemblies. The separation (height) between the frontward portions of respective top and bottom legs keeps the rearward portions of the legs inside the nose from shifting position and being inserted improperly.

The embodiment can be wiggled into the nose and can be pulled straight out. This embodiment can, but is not limited to, be made with a single gold-plated 0.020 gauge. spring steel wire, with wire ends welded together, and silicone-covered ledges. If fabricated as such, my insert can weigh less than one gram. Spring steel can allow the legs to be spread, if desired, by hand or pliers.

3. Description of Other Embodiments of the Invention

Another embodiment of my nasal insert is shown in FIG. 3. Ledges (9b and 10b) are peripherally bulbous, and can be positioned interior-to the limen nasi ridges, similar to the previous embodiment. Bulbous catches (7b and 8b) rest against the interior portion of the feet of the columella, like the previous embodiment. When worn, bulbous catches provide a more secure or varied hold, but they may also be harder to insert catches should not extend much below the bottom legs or they could inadvertently catch the sensitive floor of the sills.

Another embodiment of my nasal insert is shown in FIG. 7. The legs are bent peripherally behind the catches (7c and 8c) and the ledges (9c and 10c) are bent back medially. When worn, the ledges are flat so they can fit against the limen nasi ridges. This extensively lifts the ridges, providing for major airways, but also distorts the external shape of the nose, while worn. Many prior art nasal inserts lift the ridges nonspecifically, but in a similar manner.

In this embodiment, the bridge and legs round into each other (not notated). When worn, this provides for a rounder appearance than the angular bridge/leg connections shown in other figures. Most figures have been drawn with angular bridge/leg connections for visual clarity.

Another embodiment of my nasal insert is shown in FIG. 8. The ledges (9d and 10d) stand above the bottom legs (5d and 6d). Extra material extends between the bridges (1d and 2d) and between the legs, in front of the catches (7d and 8d), for a varied cosmetic appearance. The top legs (3d and 4d) are phantom rearward of the catches.

Another embodiment of my nasal insert is shown in FIG. 9. The legs (3e, 5e, and 4e, 6e) are rounded vertically (up/down) between the catches (7e and 8e) and ledges (9e and 10e). This rounding may provide for a larger airway between, and less so above and below, the legs. This edge roundness can only lift, not catch behind, the straight limen nasi ridges. The curvatures (17e and 18e) are only cosmetic variations of my insert.

Another embodiment of my nasal insert is shown in FIG. 10. The legs terminate rearward at the catches (7f and 8f). The peripheral sides of the legs support prior art adhesive (26). The adhesive is of a type to adhere to prior art tubing. Prior art tubing (20) with sculpted rings (21) act as continued legs and ledges respectively. Only right-hand-side tubing, ring and adhesive are notated. Small diameter tubing may also allow room air in the nare airway external and medial to the tubing.

Other similar embodiments of my nasal insert (not shown) may be attached to prior art tubing in a variety of prior art ways. These ways include, but are not limited to, adhesive, knobs, wire kinks, or loops.

Another embodiment of my nasal insert is shown in FIG. 11. The ledges (9g and 10g) support the insert in the nose without the catches. This embodiment is very easy to insert. However, this insert may not stay positioned in some wearers, like those with plentiful vestibule hair.

Another embodiment of my nasal insert is shown in FIG. 12. it does not have ledges or legs rearward of the catches.

The bottom legs (5h and 6h), frontward of the catches are notated. In this embodiment, the legs do not extend behind the catches. The catches (7h and 8h) support the insert in the nares. The purpose of this embodiment may be cosmetic (to appear as two nose rings), or used in a yet unspecified manner.

4. Symmetry, Materials, Wearers, and Dimensions

The embodiments shown in FIGS. 1A, 3, 7, 8, 9, 10, 11, and 12 are all drawn to the same scale and same side perspective view. FIG. 1A, and FIG. 1A shown in a wearer in FIGS. 4 and 5, are all drawn in the same scale to each other, and to a human nose. All measures of the embodiment in FIGS. 1A, 4, and 5 may be calculated from drawing FIGS. 4, and 5. In example, if the human nose in FIG. 4 were to have a nosetip-to-ala measurement of 38 mm, then the bottom bridge width would be 17 mm, because {a measure= [(38 mm tip to ala)÷(mm tip to ala in drawing)]×(mm of the measure in drawing)}. All measures, including diameters, are proportional thereon.

Because FIGS. 3, 7, 8, 9, 10, 11, and 12 are drawn to the same scale as FIG. 1A, they may be reconstructed into a workable device, by one skilled in the art, from the drawings and specification.

Embodiments of my nasal insert, like a wearer's nose, are majorly symmetrical. That is: right-hand-side parts are majorly the same as left-hand-side parts, except opposite hand.

Rigid, thick, or heavy materials may be used, but to no advantage. Resilient, thin, lightweight materials may ease insertion, provide comfort, and be barely visible. Materials that may be used to form the bridge and legs include but are not limited to nylon, titanium, or spring steel with gold or silver plating. Catches and ledges may be made of similar materials, or more flexible materials including, but not limited to, silicone or rubber.

Wearers may include any living creature with a pair of feet of the columella or a pair of limen nasi ridges.

The interior side of the entire post of the columella may seem to be available to lock a catch, but catching the post has big disadvantages: For one, the post's width is quite variant from person to person, so any catch behind or on the post may squeeze the septum, causing discomfort. Also there is no anteroposterior (lip-to nosetip) restriction on the post that would keep an insert from shifting in the nose. Both of these are disadvantages of the Breathe Relief nasal ring (discussed at the end of BACKGROUND OF THE INVENTION). None of the embodiments of my inserts need to catch the post of the columella or touch or press against the septum.

CONCLUSION

My nasal insert stays positioned in a wearer's nose because the catches can rest behind the feet of the columella and/ or the ledges can rest behind the limen nasi ridges.

The catches are each of a size and shape to rest against the internal side of a corresponding foot of the feet of the columella. The top/bottom bridges are of a size and shape to transcend the columella/feet of the columella respectively. The height between the frontward portions of the legs is vertically tall for stability: to keep the catches and ledges in place. The frontward portion of the top/bottom legs rearwardly fixedly attach to the respective top/bottom bridge's opposite side edges. The legs are elongated members of a size and shape to substantially insert their rearward ends into the wearer's nares. The legs fixedly support the catches and ledges. The area between top and bottom legs, between the catches and the ledges, is open to allow for a large airway. The ledges are of a size and shape to receive internal side of the wearer's limen nasi ridges. Specific embodiments may have ledges, or catches, or both. Some embodiments can use prior art nasal tubing and related apparatus to provide the bridge, the legs, the ledges, or combination thereof.

The stabalizing height between the frontward portions of respective top and bottom legs is unique to my nasal insert: Catches that only rest behind/internal-to the feet of the columella are unique to my nasal insert. The ledges that catch behind/internal-to the limen nasi ridges are also unique to my nasal insert.

I claim:

1. A nasal insert comprising:

a top bridge having opposite ends;

a bottom bridge having opposite ends;

a pair of substantially straight top legs, each having a rearward end and a frontward end;

each said frontward end of each said top leg fixedly attached to opposite side rearward ends of said top bridge's said ends;

a pair of bottom legs, each having a rearward end and a frontward end;

each said frontward end of each said bottom leg fixedly attached to opposite side rearward ends of said bottom bridge's said ends; and a means to attach each said rearward end of said top leg to a same side said rearward end of said bottom leg; wherein:

said legs are of a size and shape to substantially rearwardly insert into the wearer's pair of nares; and the height from said top bridge to said bottom bridge is substantially the anteroposterior length of a wearer's naris opening.

2. The nasal insert according to claim 1, wherein:

said means is a pair of catches, each said catch projecting medially and is of a size and shape to rest behind the internal side of a corresponding foot of the wearer's pair of feet of the columella.

3. The nasal insert according to claim 1, wherein:

said rearward end of said top legs having a downward side;

said rearward end of said bottom legs having an upward side;

said means is a pair of ledges, each fixedly attached to opposite sides of said downward side and said upward side; and each ledge of said pair of ledges is of a size and shape to rest behind the internal side of a corresponding ridge of the wearer's pair of limen nasi ridges.

4. The nasal insert according to claim 3, further comprising:

a pair of catches, each fixedly attached medially, substantially midway between said frontward and said rearward ends of an opposite side said bottom leg; and each catch of said pair of catches is of a size and shape to rest behind the internal side of a corresponding foot of the wearer's pair of feet of the columella.

5. A nasal insert support system, for securing said system in a wearer's nose, including:

a pair of substantially straight top legs extending rearwardly from opposite ends of a top bridge;

a pair of bottom legs extending rearwardly from opposite ends of a bottom bridge; and a pair of means, each attaching same side rearward ends of said top legs and said bottom legs;

such that when worn by the wearer:
   the frontward portions of said top legs and said bottom legs are at a vertical distance apart substantially the anteroposterior length of a wearer's naris openings, and
   said frontward portions extend from inside the wearer's nose to inferior to the wearer's columella, such that said length antiposteriorly confines said insert about the wearer's pair of naris openings.

6. The nasal insert support system according to claim 5, such that:
   said means are ledges; and each said ledge is for resting behind the interior surface of a limen nasi ridge of the wearer's pair of limen nasi ridges.

7. The nasal insert support system according to claim 6, such that said ledges are for internally supporting apart the wearer's lateral nasal walls.

8. The nasal insert support system according to claim 6, further including a pair of catches, such that:
   each said catch is for resting behind the interior surface of a foot of the wearer's pair of feet of the columella.

9. The nasal insert support system according to claim 5, further including a pair of catches, such that: said means are catches;
   and each said catch is for resting behind the interior surface of a foot of the wearer's pair of feet of the columella.

* * * * *